(12) United States Patent
Manke et al.

(10) Patent No.: US 6,738,052 B1
(45) Date of Patent: May 18, 2004

(54) DEVICE AND METHOD OF OPERATING TECHNICAL MEDICAL APPARATUS

(75) Inventors: Joachim Manke, Löhnberg (DE); Gerhard Schumacher, Butzbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 594 days.

(21) Appl. No.: 09/160,744

(22) Filed: Sep. 25, 1998

(30) Foreign Application Priority Data

Sep. 26, 1997 (DE) .......................................... 197 42 637

(51) Int. Cl.[7] .......................... G09G 5/00; A61M 1/14; A61M 37/00
(52) U.S. Cl. ...................... 345/177; 345/719; 422/44; 604/4; 604/5
(58) Field of Search ...................... 604/4–6; 422/44; 345/173, 156, 169, 174, 177, 965, 970, 719, 720

(56) References Cited

U.S. PATENT DOCUMENTS

| | | | | |
|---|---|---|---|---|
| 5,295,062 A | * | 3/1994 | Fukushima | 345/354 |
| 5,589,856 A | * | 12/1996 | Stein et al. | 345/173 |
| 5,609,770 A | * | 3/1997 | Zimmerman et al. | 210/739 |
| 5,614,993 A | * | 3/1997 | Smith et al. | 345/173 |
| 5,620,608 A | * | 4/1997 | Rosa et al. | 210/143 |
| 5,656,804 A | * | 8/1997 | Barkan et al. | 235/439 |
| 5,757,359 A | * | 5/1998 | Moriomoto et al. | 345/156 |
| 5,858,239 A | * | 1/1999 | Kenley et al. | 604/4 |
| 5,881,723 A | * | 3/1999 | Wallace et al. | 128/204.21 |
| 5,907,319 A | * | 5/1999 | Hashimoto et al. | 345/173 |
| 5,956,020 A | * | 9/1999 | D'Amico et al. | 345/173 |
| 5,956,023 A | * | 9/1999 | Lyle et al. | 604/6 |
| 5,978,016 A | * | 11/1999 | Lourette et al. | 348/64 |
| 6,284,131 B1 | * | 9/2001 | Hoggard et al. | 210/143 |

FOREIGN PATENT DOCUMENTS

| | | |
|---|---|---|
| DE | 41 38 453 A1 | 5/1992 |
| EP | 0 623 357 A1 | 11/1994 |

* cited by examiner

Primary Examiner—Steven Sax
Assistant Examiner—Thomas J Joseph
(74) Attorney, Agent, or Firm—Kenyon & Kenyon

(57) ABSTRACT

The present invention relates to a device for operating technical medical apparatus, especially dialysis apparatus, with a display screen and a touch screen surface and with a means for displaying and/or altering characteristic treatment data. The invention simplifies handling of technical medical apparatus and reduces the probability of operating errors by providing a second means for displaying characteristic symbols for the components of the apparatus, thereby allowing manipulation of the characteristic treatment data by touching the symbols on the touch screen surface. The invention also entails a method of operating technical medical apparatus.

21 Claims, 2 Drawing Sheets

DEVICE AND METHOD OF OPERATING TECHNICAL MEDICAL APPARATUS

FIELD OF THE INVENTION

The present invention concerns a device for operating technical medical apparatus, especially dialysis apparatus, with a display screen and a touch screen surface and with means for displaying and/or altering characteristic treatment data. This invention also concerns a method of operating technical medical apparatus.

BACKGROUND OF THE INVENTION

Display screen units with touch screen surfaces for operation of technical medical apparatus are known. In general, such operating units are used to inquire about actual patient values or machine parameters by touching an appropriate field on the touch screen surface or to enter corresponding setpoints.

European Patent No. 623,357 describes a device and a method of dialysis where the interface between the apparatus and the user is implemented in the form of such a touch screen monitor. The monitor serves to query and enter characteristic dialysis parameters, such as pumping speed, ultrafiltration rate or the conductivity of the dialysate. To enter a setpoint, the operator must touch a field on the monitor designated with the name of the parameter accordingly, ultimately arriving at a screen view where a corresponding value or a profile can be defined. A generic device and a generic method are disclosed in U.S. Pat. No. 5,609,770, where the dialysis parameters of interest are likewise selected with the help of a touch screen monitor. After the selection is made, a desired setpoint can be assigned to the parameters, with the selection of parameters as well as the inputting of values taking place by touching the surface accordingly. Because of the multitude of variable dialysis parameters, a display screen view contains a correspondingly large number of selectable fields, which makes rapid and reliable operation of the apparatus difficult. Working without mistakes is also impaired by the fact that the fields are all the same size and can be differentiated only on the basis of their designation. It is thus possible to touch the wrong fields on the touch screen surface, especially when working under time pressure, and thus, for example, enter a parameter setpoint incorrectly, which can have considerable consequences in terms of risk for the patient during treatment.

OBJECT OF THE INVENTION

The object of the present invention is to simplify the handling of technical medical apparatus and reduce the probability of operating errors.

SUMMARY OF THE INVENTION

Starting from a generic device and a generic method, the object of the invention is achieved by a device for operating a technical medical apparatus comprising a display screen and a touch screen surface and a first means for displaying and/or altering characteristic treatment data. In addition, a second means are provided for display of symbols characteristic of the components of the apparatus, where the first means can be controlled by touching the symbols on the touch screen surface. This makes it possible to largely rule out any confusion of symbols due to inadequate differentiation of the fields of the touch screen surface to be touched. Instead, by simply touching the respective symbol of the component to be influenced, the display of the corresponding data, e.g., in a control field, is activated. Such a graphical user surface permits safe and reliable use of a dialysis machine, for example. The medical personnel will very quickly become familiar with the scope of the device according to this invention due to these characteristic symbols, thus reducing the familiarization period and also increasing reliability in operation.

It is especially advantageous if at least one complete dialysis cycle can be displayed with the symbols for the components contained in the cycle. Either the dialysis fluid cycle or the blood cycle or both may be displayed, with the components contained therein, such as pumps, cut-off devices, sensors or the dialysis machine itself can be represented by means of characteristic symbols. Displaying the entire cycle facilitates the user's orientation in selecting one or more components of the dialysis cycle. This minimizes the probability of confusing different pumps, cut-off devices or heating devices, for example. It is also possible that only a portion of the components of a medical technical apparatus, in particular a dialysis apparatus or a dialysis circulatory system, can be depicted. In this context, two or even more device components of any kind, as well as their functional interrelationship, can be depicted. For example, it is conceivable that the dialyzer and the blood pump, as well as the hose line connecting the two components can be indicated using the second means. The selection of the combinations of components or segments to be indicated from the respective entire installation can be made according to the basic settings of the apparatus, or they can be set by the operator according to need. By depicting the functional connections of the interrelationships, the mode of operation for these components is made easier.

It is also possible that only portion of the components of a medical technical apparatus, in particular a dialysis apparatus or a dialysis circulatory system, can be depicted. In this context, two or even more device components of any kind, as well as their functional interrelationship, can be depicted. For example, it is conceivable that the dialyzer and the blood pump, as well as the hose line connecting the two components can be indicated using the second means. The selection of the combinations of components or segments to be indicated from the respective entire installation can be made according to the basic settings of the apparatus, or they can be set by the operator according to need. By depicting the functional connections of the interrelationships, the mode of operation for these components is made easier.

In another embodiment of this invention, the first and second means are designed so that the symbols can be displayed simultaneously and the respective treatment data can be displayed and/or altered. This makes it possible to avoid accidentally changing a setpoint or entering an actual value because the symbol of the component itself and the parameter to be changed are always displayed simultaneously.

The treatment data that can be displayed and/or changed by the first means may include the designation as well as setpoints and/or actual values and/or limit values of the instrument parameters and/or patient parameters. Whereas in a monitoring mode, essentially the actual values of the characteristic data of the components are queried, but in another operating mode of the device according to this invention, specific changes can be made in setpoints. This makes it possible to define not only individual setpoints but also a time dependence of the setpoints and thus a setpoint profile. Likewise, it is possible to set limit values for the characteristic data which, if maintained, will reliably prevent a hazardous operating state. If the limit values are reached, this may be signaled visually or acoustically or it may lead to a shutdown of the apparatus or cause cut-off devices to close. The data that can be displayed and/or changed by the first means may also include other parameters and values concerning, for example, the course of the dialysis treatment so far or the storable program data from preceding treatments of various patients.

It is especially advantageous if the means for changing the treatment data and the means for displaying the treatment data can be controlled simultaneously by touching the symbols. This generates control surfaces, for example, which display the current actual values of the corresponding parameters simultaneously and also include, for example, fields marked with arrows for corresponding changes in setpoints. Changing the data includes not only changing the setpoint but also complete startup or shutdown of a component or a function unit of the apparatus, for example.

It is likewise possible for the treatment data to be displayed first after touching the characteristic symbols for the components of the medical apparatus and for the means for altering the data to be controllable by appropriate touch of the displayable treatment data. Thus, after touching a symbol once, first only the data are displayed, and it is necessary to touch the touch screen monitor again only in the event the data must be changed.

The components of the technical medical apparatus that can be displayed by means of symbols may include blood and dialysate pumps and/or sensors and/or means for processing the dialysate. The sensors may be designed as both temperature and pressure pickups. It is likewise possible for the dialysis machine itself or cut-off devices such as valves or clamps or even heating devices to be displayable.

It is especially advantageous if several of the respective treatment data can be displayed and/or changed simultaneously by touching multiple symbols. In this way it is possible, for example, to obtain a set of actual values or a list of setpoints by touching several symbols or all symbols. It is likewise possible in this way to obtain a profile of the actual value trends in the treatment administered previously or other past treatments.

In another embodiment of this invention, the first means are designed so that a time dependence of the treatment data can be defined. In this way it is possible to define setpoint profiles, so that the success of the treatment can usually be improved in comparison with fixed predetermined setpoints within the context of a dialysis treatment. The setpoints, for example, can be entered accordingly with the time stipulations in the form of a table or a similar list. It is also possible for the user to predefine a desired course of the setpoint as a function of time by touching a corresponding field on the touch screen surface. In this case a computer unit determines the desired setpoints to be reached after a preselectable dialysis time.

It is especially advantageous if the touch screen function can be turned off after a period of time has elapsed after manipulating or touching the touch screen surface. Consequently, the touch screen function is switched off when a defined period of time has elapsed since the last operation or the last manipulation of the touch screen surface, thereby preventing any negative effects due to inadvertent touching. In particular, there can then no longer be any inadvertent change in display or even a change in the setpoints for patient parameters or instrument parameters. It is also possible for a display comprising a selection of characteristic data to be generated simultaneously or after a time lag. Thus, a survey display of only relevant data can be generated, making it easy for the operator to monitor a treatment process and clearly detect malfunctions. The selection of characteristic data that can be displayed in this way can be varied by the user or may be predetermined by the apparatus and depend, for example, on the type of treatment. An especially simple display is achieved when characteristic data are selected in an enlarged display.

The present invention also concerns a method of operating a technical medical apparatus, in particular a dialysis machine. The characteristic treatment data can be displayed and/or altered by a display screen with a touch screen surface in a first screen view, and in at least one second display screen view, the symbols characteristic of the components of the dialysis machine are displayed. The first display screen view is generated by touching these symbols. The method according to the present invention thus requires only that the user touch the desired symbol of the component of which either the actual value or another parameter is to be called up or a setpoint is to be changed. After touching the characteristic symbol, the desired actual values or other data are displayed in a corresponding screen view. Instead of displaying the data, it is likewise possible for a change in the data to be enabled. This is the goal in particular when the actual values of the parameters are always displayed together with the symbols of the components of the apparatus and when renewed display of these values is not necessary. After displaying or altering the parameters, the first screen view may be closed, and the symbols of the components of the apparatus are displayed again, for example.

In another embodiment of this invention, a screen display is generated by touching several symbols simultaneously or in succession, thus permitting simultaneous display or alteration of multiple treatment data. Thus, for example, the actual values of all treatment parameters may be displayed simultaneously and thus can be monitored easily.

According to another embodiment of the present invention, touching the symbols generates the display of the corresponding treatment data, and touching the displayed treatment data generates another screen display which makes it possible to change these data.

It is especially advantageous if the symbols of the components of the apparatus are always displayed simultaneously with the respective actual values of the parameters. Such an embodiment of the method permits an overview of the current data without requiring intervention by the treating personnel. In this case it is sufficient if touching the corresponding symbols does not lead to renewed display of the actual value but instead permits a change in the corresponding setpoint or other data, for example.

In another embodiment of the present invention, touching the symbols generates a screen view by means of which the time dependence of one or more of the treatment data is displayed. For example, if it is necessary for the ion concentration of a dialysis solution to be variable over time, the time dependence of this setpoint can also be entered by touching a corresponding symbol.

BRIEF DESCRIPTION OF THE DRAWINGS

Additional advantages and details of the present invention will become clear from an embodiment illustrated in the drawings, which show.

DETAILED DESCRIPTION OF THE PREFERRED EMBODIMENT

Figure 1:
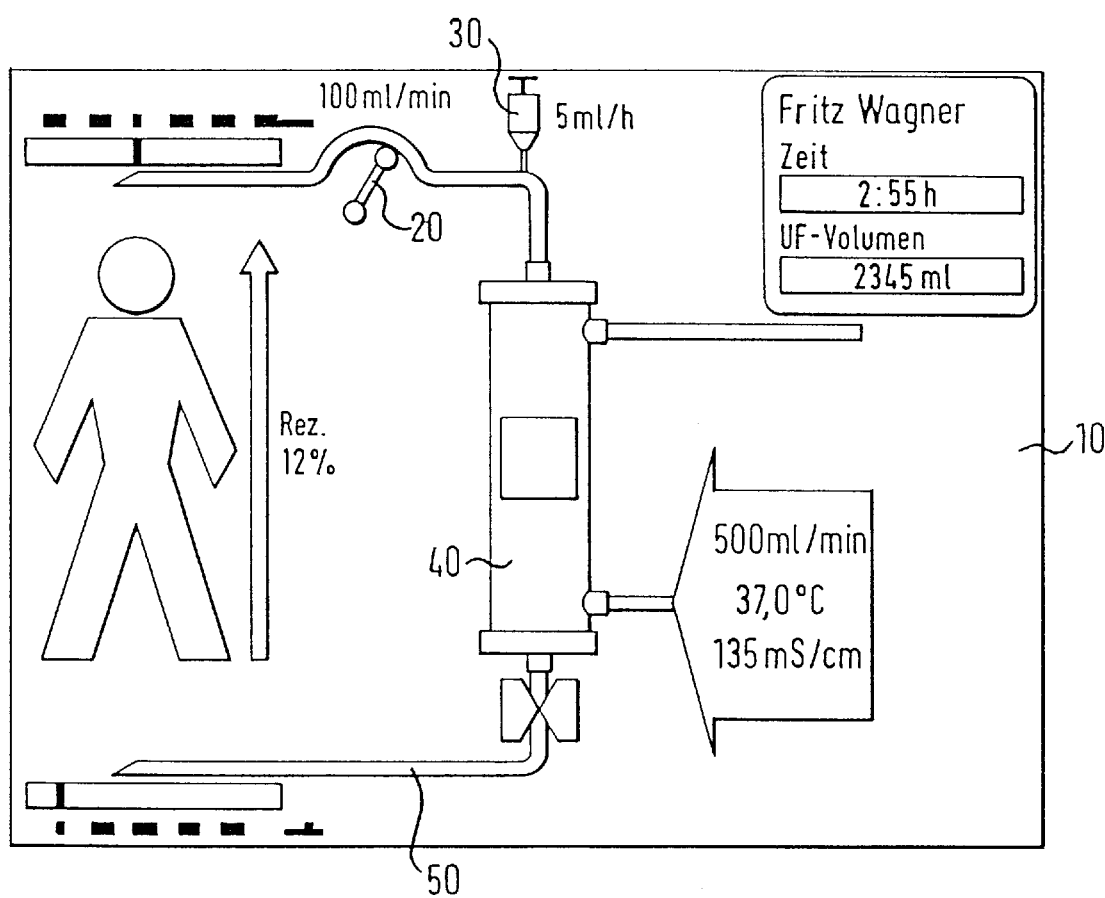
FIG. 1: a display screen view with a symbolic representation of the components of a dialysis cycle.

FIG. 1 shows the touch screen surface 10 of the device according to the present invention with the symbols for a blood pump 20, an injection pump 30 and dialyzer 40. These components are parts of extracorporeal cycle 50 which is operated in double-needle mode. The values shown next to dialyzer symbol 40 indicate the actual values for the volume flow, temperature and conductivity of the dialysis fluid supplied.

For example, if the parameters of the blood pump of dialysis cycle 50 are to be displayed or changed, it is sufficient to touch symbol 20 on the touch screen surface 10 to obtain a corresponding display.

Figure 2:
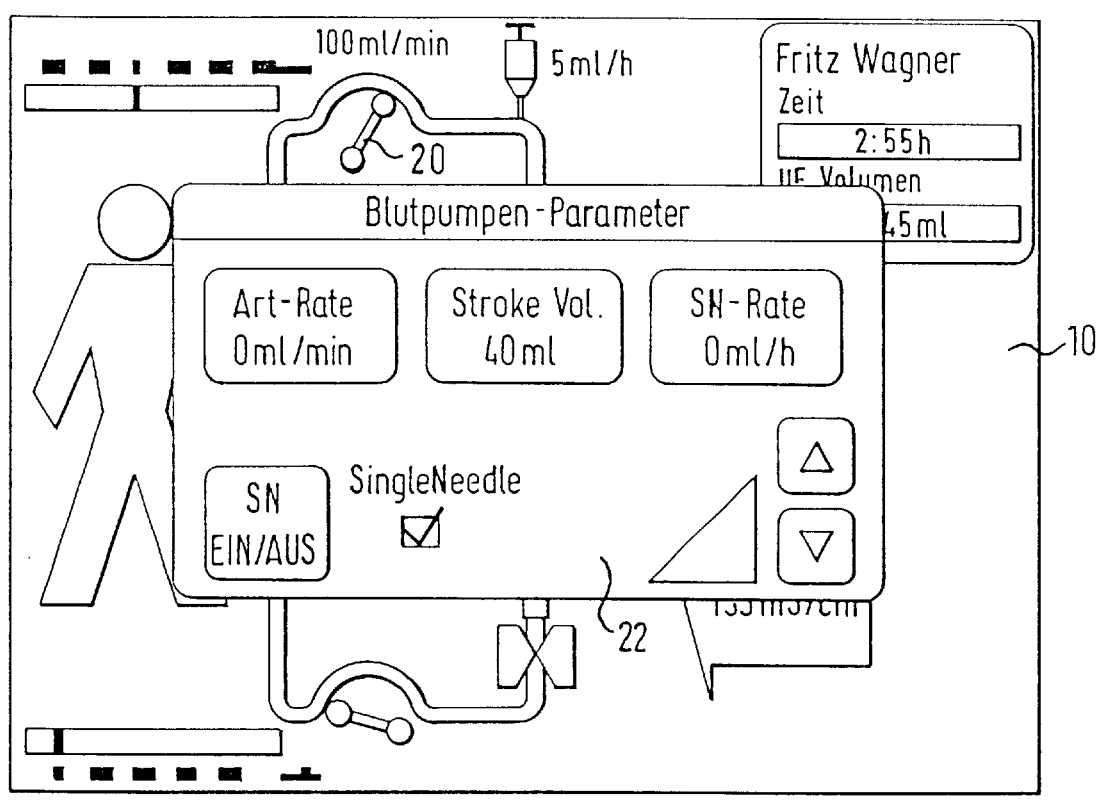
FIG. 2: a display screen view after touching the symbol for the blood pump in FIG. 1.

FIG. 2 shows the corresponding display screen view after touching symbol 20. This display screen view shows symbol 20 for the blood pump in the upper area and immediately below that a field with the respective blood pump parameters. This shows treatment data 22, with actual values or setpoints being displayed, depending on the desired operating mode, and a corresponding change in setpoints is possible by means of the arrow keys. In addition, according to the present embodiment, the operating mode of the blood pump can be changed between double-needle mode and single-needle mode. After setting the desired setpoints or reading the required actual values, the corresponding control field may either be closed automatically after a predetermined period of time or it may be closed by touching an appropriate field, thus causing the view shown in FIG. 1 to appear on touch screen surface 10 again.

The device according to the present invention and the method according to the present invention for operating a technical medical apparatus thus permit simple and reliable operation of the apparatus, e.g., a dialysis device, and also permit error-free operation of the apparatus due to the unambiguous symbols of the apparatus components and the allocation of corresponding control fields which can be generated by touching the symbols.

What is claimed is:

1. A device for operating technical medical apparatus comprising:
   a display screen;
   a touchscreen surface;
   second means for displaying a schematic representation of at least two components of the apparatus and functional relationships between the components, using a separate characteristic symbol to represent each of the at least two components of the apparatus, each of the components selected from the group consisting of pumps, cut-off devices, sensors, and heating devices, the functional relationships comprising at least one of electrical and fluid connections between the components; and
   first means for displaying and/or for allowing a user to alter treatment parameters related to the components, wherein touching by the user of the characteristics symbol displayed by the second means allows display and/or alteration via the first means of the treatment parameters corresponding to the component represented by the characteristic symbol, the parameters comprising at least one of actual and desired flow, temperature, on/off status and valve opening status.

2. The device of claim 1, wherein the technical medical apparatus is a hemodialysis unit.

3. The device of claim 2, wherein the second means is adapted to display a characteristic symbol for each component of a complete dialysis cycle.

4. The device of claim 2 wherein the second means is adapted to display a characteristic symbol for at least two components of dialysis cycle.

5. The device of claim 2 wherein the treatment parameters displayed by the first means comprise a symbol designation, value set points, actual values and limit values.

6. The device of claim 5 wherein means for altering the treatment data and means for displaying the treatment data can be activated simultaneously by touching the symbols.

7. The device of claim 5 wherein the treatment parameters include apparatus parameters.

8. The device of claim 5 wherein the treatment parameters included patient parameters.

9. The device of claim 2 wherein the treatment parameters displayed in the first means are alterable by touching the displayed parameter.

10. The device of claim 3 wherein the components for a complete dialysis cycle displayed by the second means comprise blood pump, dialysate pumps, blood sensors, dialysate sensors, heating units and means for processing dialysate.

11. The device of claim 1 wherein the first means show treatment data corresponding to at least two components depicted by symbols, said treatment data being displayed and/or being alterable simultaneously by touching the at least two corresponding symbols.

12. The device of claim 1 wherein the first means includes data on the treatment parameter as a function of time.

13. The device of claim 1 wherein the touchscreen surface is deactivated after a set time during which the touchscreen has not been manipulated.

14. The device of claim 1 wherein simultaneously the characteristic symbol is displayed and values corresponding to the treatment parameters are displayed and/or alterable.

15. A method of operating a technical medical apparatus comprising the steps of: touching a characteristic symbol for a component of the apparatus on a touch-screen surface of a device comprising: the display screen; the touchscreen surface; a second means for displaying characteristic symbols showing a schematic representation of at least two components of the apparatus and the functional relationship between the components on a touchscreen surface, each of the components selected from the group consisting of pumps, cut-off devices, sensors, and heating devices, the functional relationships comprising at least one of electrical and fluid connections between the components; and a first means for displaying and/or altering treatment parameters related to the component, wherein touching the characteristic symbol in the second means allows display and/or alteration via the first means of the treatment parameters corresponding to the symbol, the parameters comprising at least one of actual and desired flow, temperature, on/off status and valve opening status.

16. The method of claim 15 wherein the technical medical apparatus is a hemodialysis unit.

17. The method of claim 16 wherein the treatment parameters corresponding to two or more characteristic symbols are adapted to be displayed or altered simultaneously by touching the characteristic symbols simultaneously.

18. The method of claim 16 wherein the treatment parameters corresponding to two or more characteristic symbols are adapted to be displayed or altered simultaneously by touching the characteristic symbols simultaneously.

19. A method of operating a technical medical apparatus comprising the steps of: touching a characteristic symbol for a component of the apparatus on a touch-screen surface of a device comprising: the display screen; the touchscreen surface; a second means for displaying characteristic symbols showing a schematic representation of at least two components of the apparatus and the functional relationship between the components on a touchscreen surface, each of the components selected from the group consisting of pumps, cut-off devices, sensors, and heating devices, the functional relationships comprising at least one of electrical and fluid connections between the components means for displaying and means for altering treatment parameters related to the component, wherein touching the characteristic symbol in the second means allows display via the means for displaying of the treatment parameters corresponding to the symbol and wherein touching the displayed treatment parameters allows alteration via the means for altering of the treatment parameters corresponding to the symbol, the parameters comprising at least one of actual and desired flow, temperature, on/off status and valve opening status.

20. The method of claim 16 wherein the characteristic symbol is displayed simultaneously with values for the corresponding treatment parameters.

21. The method of claim 16 wherein the first means includes the parameter data as a function of time.

* * * * *